(12) United States Patent
Palermo

(10) Patent No.: US 12,622,797 B2
(45) Date of Patent: May 12, 2026

(54) VASCULAR AND AORTIC CONNECTORS WITH ROBOTIC DELIVERY AND DEPLOYMENT METHODS THEREOF

(71) Applicant: Aquedeon Medical, Inc., Sunnyvale, CA (US)

(72) Inventor: Thomas J. Palermo, San Jose, CA (US)

(73) Assignee: Aquedeon Medical, Inc., Sunnyvale, CA (US)

( * ) Notice: Subject to any disclaimer, the term of this patent is extended or adjusted under 35 U.S.C. 154(b) by 887 days.

(21) Appl. No.: 17/867,854

(22) Filed: Jul. 19, 2022

(65) Prior Publication Data

US 2022/0346994 A1     Nov. 3, 2022

Related U.S. Application Data

(63) Continuation-in-part of application No. 17/191,945, filed on Mar. 4, 2021, now Pat. No. 12,403,024.

(Continued)

(51) Int. Cl.
*A61F 2/966* (2013.01)
*A61F 2/95* (2013.01)

(52) U.S. Cl.
CPC ............ *A61F 2/966* (2013.01); *A61F 2/9522* (2020.05); *A61F 2250/0073* (2013.01); *A61F 2250/0097* (2013.01)

(58) Field of Classification Search
CPC .............. A61F 2/966–9662; A61F 2/95; A61F 2/9517; A61F 2002/9665; A61B 17/11; A61B 2017/1107; A61B 2017/1132

(Continued)

(56) References Cited

U.S. PATENT DOCUMENTS 5,700,269 A * 12/1997 Pinchuk ............... A61B 5/1076
606/198
5,776,142 A * 7/1998 Gunderson ............... A61F 2/88
606/198

(Continued)

FOREIGN PATENT DOCUMENTS

DE        102013160463       12/2014
EP          2111826 A1      10/2009

(Continued)

OTHER PUBLICATIONS

Notice of Reasons for Refusal from related Japanese Patent Application No. 2022-552863 dated Apr. 15, 2025.

(Continued)

*Primary Examiner* — Elizabeth Houston
*Assistant Examiner* — Serenity A Miller
(74) *Attorney, Agent, or Firm* — Dergosits & Noah LLP; Todd A. Noah

(57) ABSTRACT

A deployment tool and associated method are disclosed for implanting a vascular connector in a patient. The vascular connector deployment tool has a housing, an inner sheath extending distally from the housing, a floating mandrel, a vascular connector disposed coaxially about the mandrel, and an outer sheath telescopically deployed over an inner sheath. The outer sheath constrains the vascular connector around the mandrel in an insertion profile when the outer sheath is disposed over the vascular connector. The inner sheath may be rotated to cause the outer sheath to retract relative to the floating mandrel and expose sequential portions of the vascular connector. A drive disposed within the housing and coupled to a proximal end of the outer sheath translates rotational motion of the inner sheath into longitudinal motion of the outer sheath.

19 Claims, 4 Drawing Sheets

Related U.S. Application Data

(60) Provisional application No. 63/224,561, filed on Jul. 22, 2021.

(58) Field of Classification Search
USPC ....... 606/108, 191, 192, 194, 200; 623/1.11, 623/1.12
See application file for complete search history.

(56) References Cited

U.S. PATENT DOCUMENTS

| | | | |
|---|---|---|---|
| 6,019,787 | A | 2/2000 | Richard et al. |
| 6,217,585 | B1* | 4/2001 | Houser ................. A61M 29/02 606/198 |
| 6,254,593 | B1 | 7/2001 | Wilson |
| 6,352,561 | B1 | 3/2002 | Leopold et al. |
| 6,849,084 | B2* | 2/2005 | Rabkin ................. A61F 2/9662 606/108 |
| 7,879,904 | B2 | 2/2011 | Zygmunt et al. |
| 7,887,574 | B2* | 2/2011 | McFerran ................. A61F 2/95 623/1.11 |
| 8,003,069 | B2 | 8/2011 | Riebel et al. |
| 8,641,752 | B1 | 2/2014 | Holm et al. |
| 8,778,006 | B2 | 7/2014 | Faraghi et al. |
| 8,904,764 | B2 | 12/2014 | Baier et al. |
| 9,192,500 | B1 | 11/2015 | Longo et al. |
| 9,763,819 | B1 | 9/2017 | Sondreaal |
| 9,972,933 | B2 | 5/2018 | Kimura et al. |
| 10,172,732 | B2* | 1/2019 | Murphy ................. A61F 2/966 |
| 10,219,890 | B2 | 3/2019 | Madjarov et al. |
| 10,363,155 | B2 | 7/2019 | Lesmeister et al. |
| 11,684,466 | B2 | 6/2023 | Varga |
| 2003/0139805 | A1 | 7/2003 | Holmberg et al. |
| 2003/0199966 | A1 | 10/2003 | Shiu et al. |
| 2004/0044395 | A1 | 3/2004 | Nelson |
| 2005/0027305 | A1 | 2/2005 | Shiu et al. |
| 2005/0033410 | A1 | 2/2005 | Hogendijk et al. |
| 2005/0065590 | A1* | 3/2005 | Shelso ................. A61F 2/966 623/1.11 |
| 2005/0080430 | A1 | 4/2005 | Wright, Jr. et al. |
| 2005/0182475 | A1 | 8/2005 | Jen et al. |
| 2005/0288766 | A1* | 12/2005 | Plain ................. A61F 2/97 623/1.12 |
| 2006/0235501 | A1 | 10/2006 | Igaki |
| 2007/0100422 | A1 | 5/2007 | Shumer et al. |
| 2008/0097572 | A1 | 4/2008 | Sheldon et al. |
| 2008/0132993 | A1 | 6/2008 | Rasmussen et al. |
| 2008/0288042 | A1 | 11/2008 | Purdy et al. |
| 2008/0294230 | A1 | 11/2008 | Parker |
| 2009/0125097 | A1 | 5/2009 | Bruszewski et al. |
| 2009/0254165 | A1 | 10/2009 | Tabor et al. |
| 2011/0288580 | A1 | 11/2011 | Ginn et al. |
| 2012/0065590 | A1 | 3/2012 | Bierman et al. |
| 2012/0101561 | A1* | 4/2012 | Porter ..................... A61F 2/966 623/1.11 |
| 2013/0226278 | A1 | 8/2013 | Newell et al. |
| 2013/0282103 | A1 | 10/2013 | Madjarov et al. |
| 2013/0310583 | A1 | 11/2013 | Carlberg et al. |
| 2015/0066131 | A1 | 3/2015 | Luong et al. |
| 2016/0022454 | A1 | 1/2016 | Bonutti |
| 2016/0151056 | A1 | 6/2016 | Lederman et al. |
| 2016/0270936 | A1 | 9/2016 | Berra et al. |
| 2016/0287417 | A1 | 10/2016 | Bhave et al. |
| 2017/0252161 | A1 | 9/2017 | Tran et al. |
| 2017/0290690 | A1 | 10/2017 | Green |
| 2018/0000619 | A1 | 1/2018 | Longo et al. |
| 2018/0085240 | A1 | 3/2018 | Mower et al. |
| 2018/0193043 | A1 | 7/2018 | Marchand et al. |
| 2019/0008631 | A1 | 1/2019 | Stone et al. |
| 2019/0083101 | A1 | 3/2019 | Broyles et al. |
| 2019/0133748 | A1 | 5/2019 | Torales |
| 2019/0151071 | A1 | 5/2019 | Mogenson |
| 2019/0247213 | A1 | 8/2019 | Lostetter |
| 2019/0300218 | A1 | 10/2019 | Patzer et al. |
| 2019/0321207 | A1* | 10/2019 | Arbefeuille .......... A61F 2/9662 |
| 2020/0038213 | A1 | 2/2020 | Bly et al. |

FOREIGN PATENT DOCUMENTS

| | | | |
|---|---|---|---|
| JP | 201506902 | A | 5/2001 |
| JP | 2007007442 | A | 1/2007 |
| JP | 2006525074 | A | 3/2007 |
| JP | 2009523565 | A | 6/2009 |
| JP | 2012065933 | A | 4/2012 |
| JP | 2014501560 | A | 6/2014 |
| JP | 2015517850 | A | 6/2015 |
| JP | 2016137271 | A | 10/2016 |
| JP | 2018051259 | A | 6/2018 |
| JP | 2019528823 | A | 12/2019 |
| WO | 19980027894 | | 7/1998 |
| WO | 2007084762 | A2 | 7/2007 |
| WO | 2020010237 | A1 | 1/2020 |

OTHER PUBLICATIONS

International Preliminary Report on Patentability from corresponding International Patent Application No. PCT/US2022/037541, dated Jan. 24, 2024.

International Search Report and Written Opinion from related International Patent Application No. PCT/US2021/020800, dated Jun. 15, 2021.

Search Report and Written Opinion from corresponding International Patent Application No. PCT/US22/37541, mailed Nov. 4, 2022.

* cited by examiner

VASCULAR AND AORTIC CONNECTORS WITH ROBOTIC DELIVERY AND DEPLOYMENT METHODS THEREOF

RELATED APPLICATIONS

This patent application claims priority to U.S. Provisional Patent Application No. 63/224,561, filed Jul. 22, 2021, which is hereby incorporated by reference in its entirety and for all purposes. Further, this application is a continuation-in-part of U.S. patent application Ser. No. 17/191,945, filed Mar. 4, 2021, which is commonly-assigned and is also incorporated by reference in its entirety and for all purposes.

FIELD OF THE PRESENT DISCLOSURE

The invention generally relates to vascular and aortic connectors, with particular regard to deployment tools and methods for such deploying such connectors.

BACKGROUND

The circulatory system includes the aorta and other large-diameter blood vessels, as well as smaller-diameter blood vessels and capillaries. Therapeutic interventions to replace or support diseased or otherwise compromised vessels may involve the use of synthetic grafts to maintain or restore patency of the affected vessel to perfuse downstream anatomy. Although disease and other conditions are known to affect all types of blood vessels, those affecting the aorta may be more serious and more likely to result in patient death, due to the volume and pressure of blood that is pumped through the aorta. Accordingly, the example discussed below is framed in the context of aortic grafts, but it should be appreciated that the techniques of this disclosure are applicable to other portions of a patient's vasculature.

Aortic aneurysm is a serious condition that can affect any segment of the aorta. An aortic aneurysm in the abdomen is referred to as an abdominal aortic aneurysm or AAA; an aortic aneurysm in the chest cavity is referred to as a thoracic aortic aneurysm or TAA, and an aneurysm in the chest cavity on the aortic arch may be referred to as an aortic arch aneurysm. Aortic aneurysms may result from different causes, such as untreated or severe hypertension, smoking, generic disease such as Marfan's syndrome, and degenerative dilation of the aortic wall. A thoracic aortic aneurysm results from weakening of the aortic wall, leading to localized dilatation, and is a life-threatening condition. Patients with thoracic aneurysms are often asymptomatic until the aneurysm expands. The most common presenting symptoms are pain and aortic rupture. A ruptured aneurysm can cause severe internal bleeding, which can rapidly lead to shock or death.

Patients with acute dissection typically present with pain and are classed as emergencies due to the risk of the dissection rupturing the wall of the aorta, affecting the integrity of the aortic valve and, through involvement of the origins of the coronary arteries, affecting perfusion of the myocardium. Typically, a dissection of the ascending aorta that extends into the aortic arch or that involves any of the arteries of the aortic arch requires surgical insertion of a graft to replace the diseased portion of the ascending aorta and additional grafts to reestablish blood flow to each artery stemming from the aortic branch where any dissection or disease is present. The grafts may be connected to the vasculature by expanding a connector from an insertion profile to a deployed profile to secure the graft to a vessel.

The procedure may also involve inserting an additional stent that is dedicated to provide blood flow from the ascending aorta to vasculature distal of the descending aorta. Conditions affecting other portions of the patient's vasculature may also be treated in a similar manner.

Complex thoracic aortic disease encompasses acute (AAD) and chronic type A dissections (CAD), as well as aortic arch aneurysm with or without involvement of the ascending and descending aorta. Aortic dissection results from a tear in the inner layer of the wall of the aorta leading to blood entering and separating the layers of the wall. Acute aortic dissections are defined as those identified within the first 2 weeks after the initial tear, and chronic dissections are defined as those identified at times greater than 2 weeks. Aortic dissection is classified by its location and the extent of involvement of the thoracic aorta. Stanford Type A dissection affects the ascending aorta and may extend to the arch and descending thoracic aorta. Stanford Type B dissection does not affect the ascending aorta and typically involves the descending thoracic aorta, distal to the origin of the left subclavian artery. Approximately two-thirds of aortic dissections are Stanford Type A.

Treatment of complex thoracic aortic disease typically requires long and complicated open surgery. During such surgery, the patient is typically placed on a cardiopulmonary bypass pump, and the heart is stopped to allow the aorta to be clamped and operated upon. While the patient is on cardiopulmonary bypass, the patient generally is also chilled to a condition of hypothermia. The risk that the patient will not be able to survive the surgery is directly related to the duration of time that the patient spends on pump and under hypothermia.

Correspondingly, it would be desirable to provide tools and methods for deploying aortic connectors for aneurysm repair that facilitate and expedite their placement. Similarly, it would also be desirable to provide tools and methods that may be used for deploying connectors in other portions of a patient's vasculature. Still further, it would be desirable to provide tools and methods that may employed as part of a robotic delivery procedure. As will be detailed in the following materials, this disclosure satisfies these and other goals.

SUMMARY

The present disclosure is directed to a vascular connector deployment tool having a housing, an inner sheath extending distally from the housing, wherein the inner sheath is rotatable with respect to the housing, a floating mandrel, a connector coupling the floating mandrel to a distal end of the inner sheath such that the inner sheath is capable of rotation with respect to the floating mandrel, a vascular connector disposed coaxially about the mandrel, an outer sheath telescopically deployed over an inner sheath, wherein the outer sheath is configured to constrain the vascular connector around the mandrel in an insertion profile when the outer sheath is disposed over the vascular connector and a drive disposed within the housing that is coupled to a proximal end of the outer sheath and is configured to translate a rotational motion of the inner sheath into a longitudinal motion of the outer sheath.

In one aspect, the drive may be coaxially disposed over a proximal portion of the inner sheath and engages external threads on the proximal portion of the inner sheath. The drive may travel along guides in the housing that permit longitudinal motion and resist rotational motion.

In one aspect, the drive may be configured to translate a first predetermined amount of rotation of the inner sheath into a first known amount of longitudinal motion of the outer sheath. The first known amount of longitudinal motion may expose a distal portion of the vascular connector. Further, the drive may be configured to translate a second predetermined amount of rotation of the inner sheath into a second known amount of longitudinal motion of the outer sheath and wherein the second known amount of longitudinal motion exposes a proximal portion of the vascular connector.

In one aspect, the inner sheath may have an interface that extends from a proximal end of the housing as is configured to rotate the inner sheath.

In one aspect, the floating mandrel may comprise a shoulder configured to engage and resist proximal longitudinal motion of the vascular connector when the outer sheath is retracted.

In one aspect, the vascular connector may be visible through the outer sheath. Alternatively, or in addition, the outer sheath may have a marker configured to indicate a position of the vascular connector prior to retraction of the outer sheath.

In one aspect, the vascular connector may be a self-expanding connector and be able to maintain radial force at a temperature in a range of 19° C. to 37° C.

In one aspect, the floating mandrel and the inner sheath may have a guidewire lumen.

This disclosure also includes a method for implanting a vascular connector in a patient. The method may include providing a vascular connector deployment tool including a housing, an inner sheath extending distally from the housing, wherein the inner sheath is rotatable with respect to the housing, a floating mandrel, a connector coupling the floating mandrel to a distal end of the inner sheath such that the inner sheath is capable of rotation with respect to the floating mandrel, a vascular connector disposed coaxially about the mandrel, and an outer sheath telescopically deployed over an inner sheath, wherein the outer sheath is configured to constrain the vascular connector around the mandrel in an insertion profile when the outer sheath is disposed over the vascular connector. At least a distal portion of the vascular connector may be positioned within a first lumen for conducting blood of the patient. The inner sheath may be rotated to cause the outer sheath to retract relative to the floating mandrel and expose a distal portion of the vascular connector. The distal portion of the vascular connector may be secured within the first lumen by expansion of the portion of the vascular connector from the insertion profile.

In one aspect, rotation of the inner sheath may cause a drive disposed within the housing and coupled to a proximal end of the outer sheath to move longitudinally. Rotating the inner sheath may include imparting a first predetermined amount of rotation to cause a first known amount of longitudinal motion of the outer sheath, such that the first known amount of longitudinal motion exposes a distal portion of the vascular connector.

In one aspect, further operations may include advancing a second lumen for conducting blood of the patient coaxially over the deployment tool until an end of the second lumen is adjacent the opening of the first lumen. Rotating the inner sheath further to cause the outer sheath to retract relative to the floating mandrel and expose a remaining portion of the vascular connector. The remaining portion of the vascular connector may be secured within the second lumen by expansion of the portion of the vascular connector from the insertion profile. Further rotating the inner sheath may include imparting a second predetermined amount of rotation of the inner sheath to cause a second known amount of longitudinal motion of the outer sheath, such that the second known amount of longitudinal motion exposes a proximal portion of the vascular connector.

In one aspect, the first lumen is a blood vessel and the second lumen is a graft.

In one aspect, positioning at least the distal portion of the vascular connector within the first lumen may include visualizing the vascular connector through the outer sheath. Alternatively, or in addition, positioning at least the distal portion of the vascular connector within the first lumen may include using a marker that indicates position of the vascular connector prior to retraction of the outer sheath.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. As used in this document, and as customarily used in the art, the word "substantially" and similar terms of approximation refer to normal variations in the dimensions and other properties of finished goods that result from manufacturing tolerances and other manufacturing imprecisions. Finally, as used in this specification and the appended claims, the singular forms "a, "an" and "the" include plural referents unless the content clearly dictates otherwise.

Figure 1:
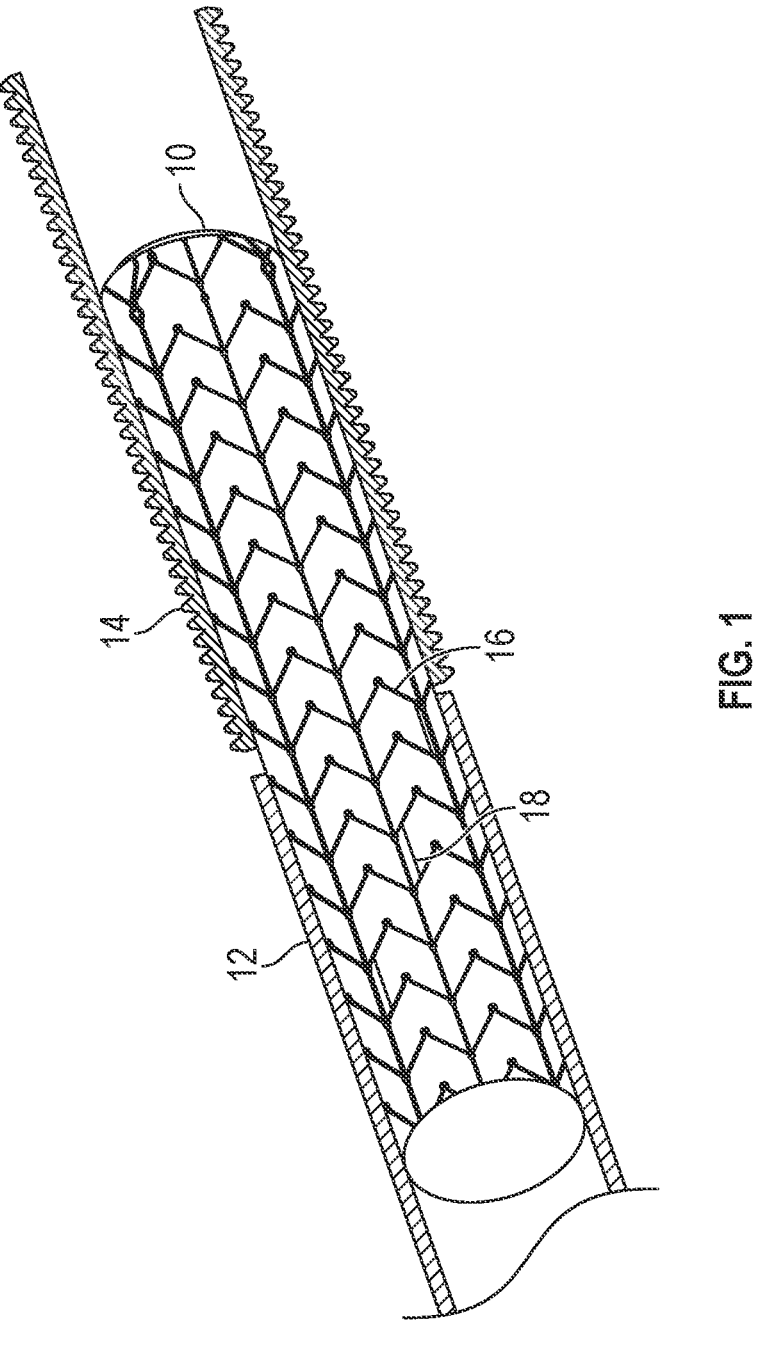
FIG. 1 schematically illustrates a vascular connector used to connect a blood vessel and a graft, according to an embodiment of the disclosure.

Referring to FIG. 1, a vascular connector 10 is shown that may be adapted for use in the aorta or other suitable locations in the patient's vasculature to help establish or restore fluid communication by joining blood vessel 12, such as one that may be dissected, to graft 14, such as a branch graft. Graft 14 may be fabricated from any suitable material or materials, such as but not limited to polytetrafluoroethylene (PTFE) or a polyester such as polyethylene terephthalate (PET), sometimes known as DACRON® brand polyester available from E. I. Du Pont De Nemours and Company of Wilmington, Del. The vascular connector 10 is expandable from a first insertion diameter to a second deployed diameter and may have any structure that allows for expansion from a first insertion diameter to a second deployed diameter and that holds vascular connector 10 securely inside vessel 12 and graft 14 in the deployed state. As one example, vascular connector 10 may include a plurality of circumferentially extending hoops 16, similar in design to a stent. The hoops 16 may be longitudinally spaced apart; and if so, adjacent hoops 16 may be connected by one or more tie bars 18. Alternately, adjacent hoops 16 are not spaced apart, but instead abut or overlap one another. In such a configuration, such adjacent hoops 16 may be fixed to one another, such as by laser welding. The hoops 16 may be fabricated from metal or other material. Each hoop 16 may have a complex shape in which the hoop 16 is fabricated from a wire, or laser cut from a tube, or otherwise manufactured such that the hoop 16 has a complex shape, such as a zig-zag, repeating Z shape, tortuous curve, or other shape. Such a shape allows the hoop 16 to expand from an insertion diameter to a deployed diameter. The zig-zag pattern of at least one hoop 16 may be continuously curved or may include straight segments connected by curved segments. In one embodiment, the zig-zag pattern of the hoops 16 may be as set forth in expired U.S. Pat. No. 4,580,568, which is incorporated herein by reference in its entirety. However, at least one hoop 16 may be configured differently.

In one embodiment, different hoops 16 may be fabricated from different materials. For example, at least one hoop 16 may be fabricated from superelastic material, such as nickel-titanium alloy, and at least one other hoop 16 may be fabricated from plastically-deformable material, such as 316L stainless steel. Adjacent hoops 16 may alternate between different materials, such that no hoop 16 is adjacent to a hoop 16 composed of the same material. In other embodiments, several hoops 16 composed of the same material may be grouped together, and at least one hoop 16 composed of a different material may be adjacent to that group. For example, a hoop 16 at an outer end of vascular connector 10 may be composed of stainless steel, and the remaining hoops 16 may be composed of superelastic material such as nickel-titanium alloy. By using hoops 16 fabricated from different materials, the vascular connector 10 takes advantage of the different properties of those different materials. For example, one or more hoops 16 fabricated from superelastic material are useful in self-expanding the vascular connector 10. One or more additional hoops 16 fabricated from a plastically-deformable material such as 316L stainless steel are useful for maintaining the lumen of vascular connector 10 open, because such material has greater resistance to hoop stress and is not susceptible to a return to a different crystal phase after expansion. In addition, such hoops 16 fabricated to be in structure configured to maintain its radial force at the temperature ranging from 19° C. to 37° C. Although the term "hoop" is used in this document, the hoops 16 need not be perfectly circular as viewed on end, and may have a different shape and curvature as suitable for a particular application. In some embodiments, the hoops 16 are substantially circular as viewed on end.

In one embodiment, the opposing ends of vascular connector 10 each expand to the same or similar diameters in the deployed state. In other embodiments, one end expands to a different diameter in the deployed state than the opposing end to allow joining a vessel 12 and graft 14 that have different diameters. The difference in diameter may be controlled by controlling the diameter of the hoops 16 in the respective ends, by providing a different mix of hoops 16 with different materials, or in any other suitable manner.

As noted above, vascular connector 10 may be used to join vessel 12 to graft 14 and it is correspondingly desirable to first deploy half the length of connector 10 into vessel 12, and then the other half of connector 10 within graft 14 to effectively connect the vessel 12 to the graft 14. Accurately deploying the proper amount of connector 10 into both the vessel 12 and graft 14 is advantageous since too much of the connector 10 being deployed in the vessel 12 risks the connection within the graft 14 while too little of the connector 10 being deployed in the vessel 12 risks connection within the vessel 12, and it should be appreciated that both scenarios can be catastrophic to the patient. Appropriate visualization greatly facilitates any open surgical procedure, so the techniques of this disclosure improve the ability to accurately assess the proper amount of connector 10 within the vessel 12 or branch graft 14 during the operation as discussed in detail below.

Figure 2:
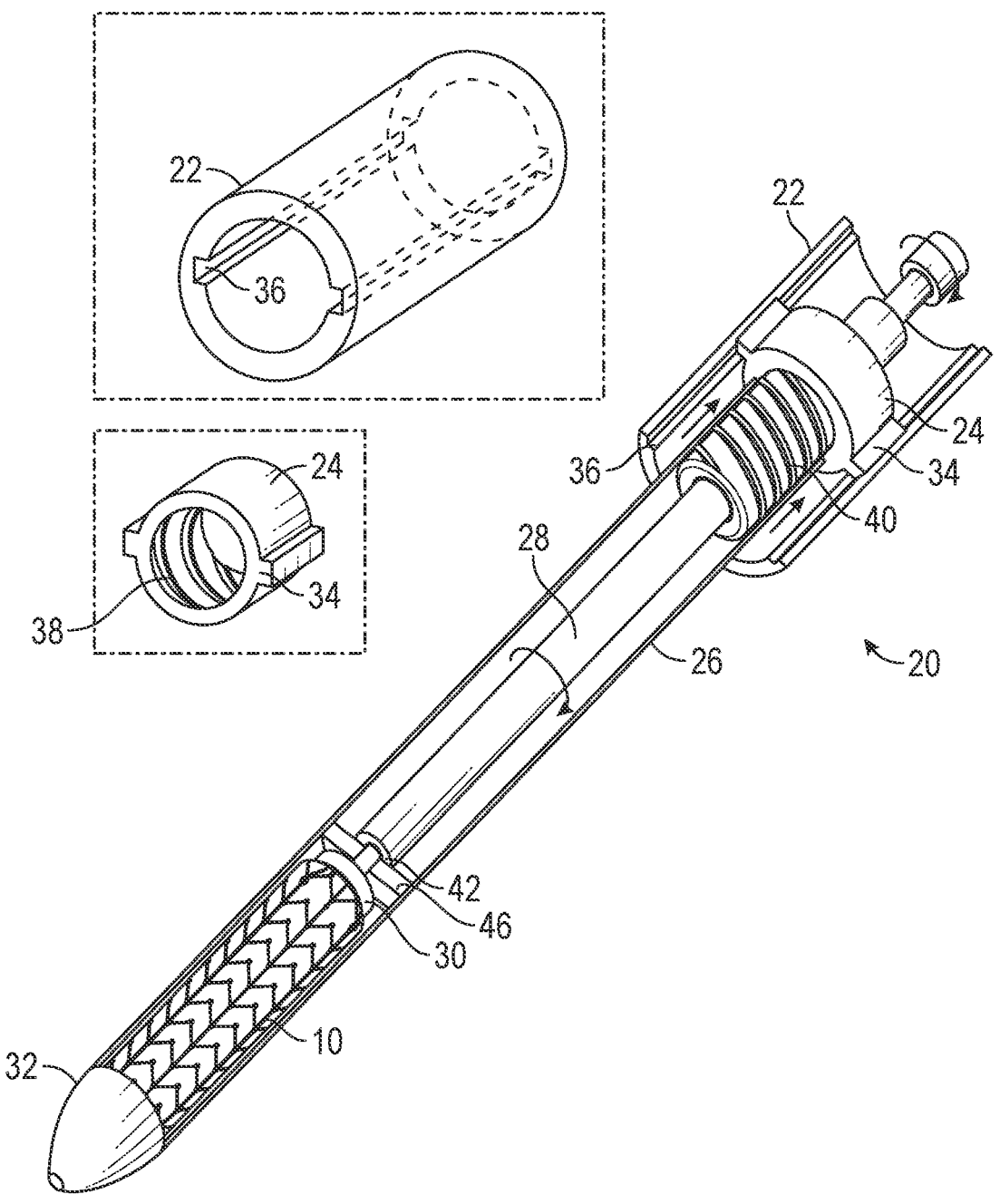
FIG. 2 schematically illustrates a partial cross-sectional view of a deployment tool for positioning and placing a vascular connector, according to an embodiment of the disclosure.
Figure 3:
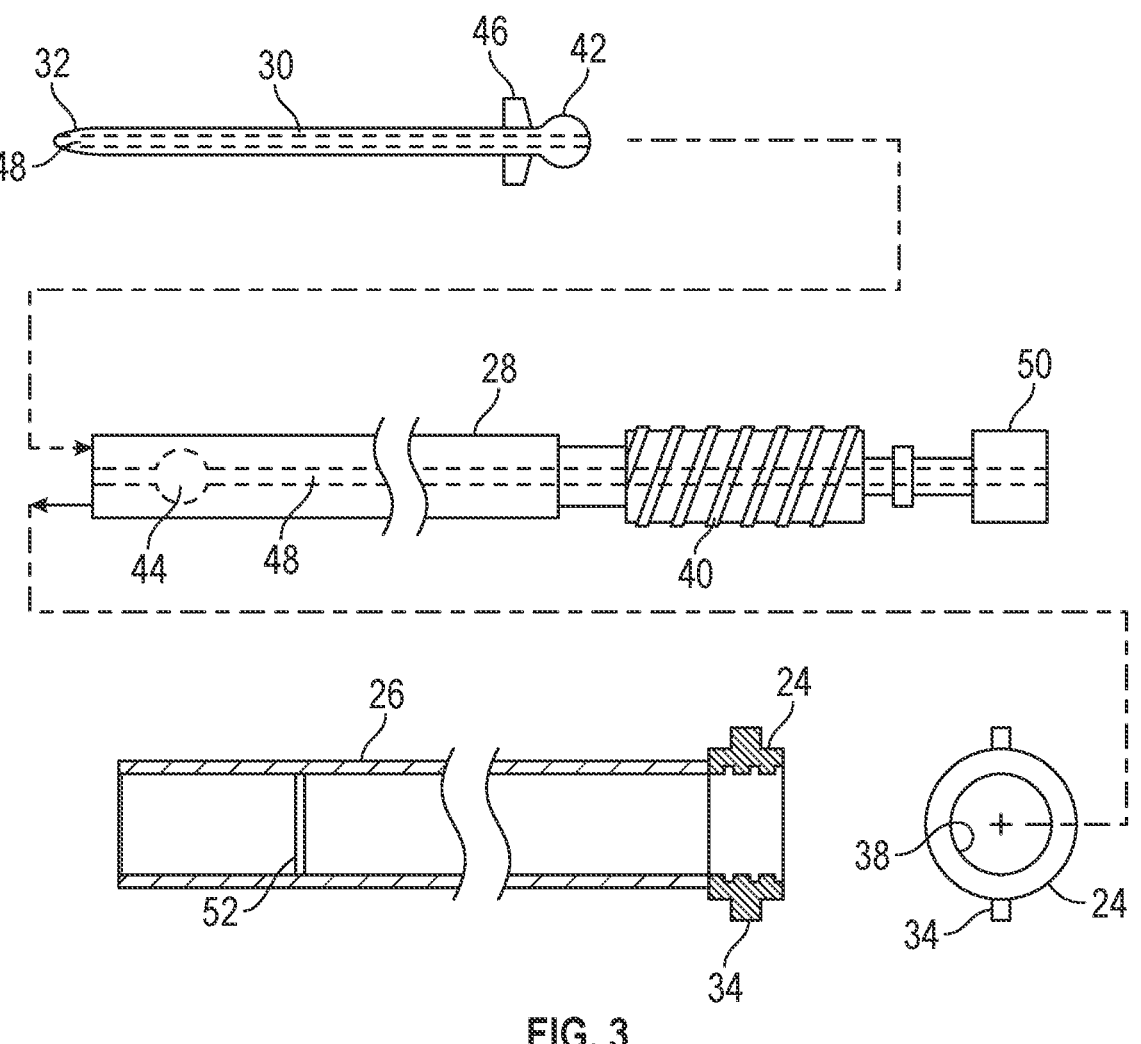
FIG. 3 is an exploded view that schematically depicts the coaxial relationship of the components of the deployment tool of FIG. 2, according to an embodiment of the disclosure.

Accordingly, vascular connector 10 or a connector having similar characteristics may be deployed using deployment tool 20, schematically depicted partially in section in FIG. 2 and in an exploded view in FIG. 3 that indicates the coaxially relationship of the various components. Deployment tool 20 includes housing 22 containing nut drive 24 that is coupled to outer sheath 26 and is driven by rotation of inner sheath 28. At the distal end of deployment tool 20 is floating mandrel 30 with a blunt, atraumatic tip 32. As indicated, vascular connector 10 is wrapped around mandrel 30 and held in its compressed configuration at least partially against the mandrel by outer sheath 26. Outer sheath 26 is telescopically disposed over inner sheath 28, floating mandrel 30 and connector 10 and is selectively retractable via rotation of inner sheath 28. In particular, nut drive 24 has projections 34 that travel longitudinally within guides 36 of housing 22, with these components shown in the detail insets of FIG. 2. Nut drive 24 also features internal screw threads 38 that engage external threads 40 on a proximal portion of inner sheath 28, functioning as a leadscrew to impart a desired longitudinal motion in response to rotation of inner sheath 28. Since outer sheath 26 is coupled to nut drive 24, proximal movement of nut drive 24 produces a corresponding withdrawal of outer sheath 26 to expose and deploy connector 10 as described in further detail below. A coupling joint of ball 42 and socket 44 as depicted in FIG. 3, maintains the relative longitudinal position of floating mandrel 30 to inner sheath 28 but allows free rotation of inner sheath 28 during deployment. Shoulder 46 has an outer diameter similar to the inner diameter of outer sheath 26 to resist undesirable proximal movement of connector 10 during deployment when outer sheath is retracted. In alternative embodiments, similar functionality can be provided by a shoulder structure positioned adjacent the distal end of inner sheath 28. Guidewire lumen 48 is provided through floating mandrel 30 and inner sheath 28 to facilitate advancement of deployment tool 20 to a desired position within the patient's vasculature.

In one embodiment, interface 50 at the proximal end of inner sheath 28 is configured to mate with a robotic arm or similar tool so that delivery of connector 10 can be accomplished under machine control. Notably, a precise amount of rotation can be applied to inner sheath 28 to achieve a similarly precise amount of retraction of outer sheath 26. As will be appreciated, this facilitates the multi-stage delivery of connector 10 noted above. However, inner sheath 28 may also be driven manually in other embodiments and may have a handle or other actuator adapted for that purpose.

Outer sheath 26 may cover the entire length of vascular connector 10 before retraction and it may be desirable to sequentially deploy different predetermined portions of connector 10 based its characteristics and the objectives of the procedure. For the sake of illustration and without limitation, a distal 3.5 cm portion of a 7 cm connector may be deployed in a patient's native vessel 12 during a first stage and then after suitable positioning, the remaining proximal 3.5 cm portion may be deployed in graft 14. The distances can be varied as warranted depending on the length of the connector 10 and the proportion desired to be covered. Outer sheath 26 may be formed from suitable polymeric materials, such as nylon (polyamide), urethane, polypropylene, as well as polyamide co-polymers such as, for example, polyether block amides (PEBAX®), or others may be employed. In some embodiments, outer sheath 26 is sufficiently translucent to allow visualization of connector 10 to help ensure proper placement for example by using a substantially clear or transparent polymer. It should be recognized that clarity is relative and for the purposes of this disclosure, any difference in optical properties that enables connector 10 to be visualized through outer sheath 26 may be used. Alternatively, outer sheath 26 may have a marker 52 to indicate the relative position of connector 10. For example, marker 52 may represent the midpoint of connector 10 prior to any retraction of outer sheath 26.

As will be appreciated, the controlled retraction of outer sheath 26 facilitates accurate deployment of connector 10 within vessel 12 and graft 14. For example, a procedure involving the symmetrical deployment of connector 10 may be accomplished by positioning deployment tool 20 so that connector 10 is deployed within vessel 12 (also potentially under robotic control) and imparting a known amount of rotation to inner sheath 28 so that one half of connector 10 is exposed and deployed. Subsequently, after graft 14 is positioned over the proximal portion of connector 10, another known amount of rotation may be imparted to inner sheath 28 to complete deployment. Once more, it should be appreciated that rotation of inner sheath 28 may also be performed manually to deploy connector 10 if desired.

Figure 4:
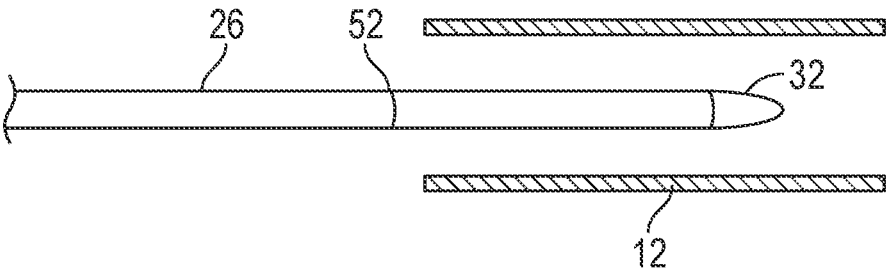
FIG. 4 schematically illustrates positioning a vascular connector within a blood vessel, according to an embodiment of the disclosure.
Figure 5:
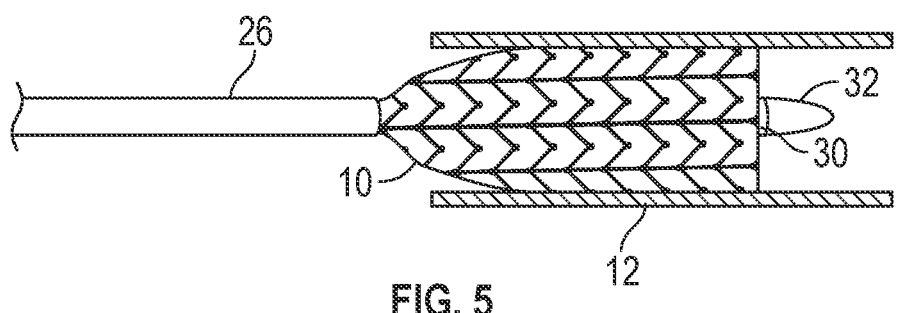
FIG. 5 schematically illustrates retracting an outer sheath of the deployment tool to allow expansion of a distal portion of the vascular connector to secure it within the blood vessel, according to an embodiment of the disclosure.
Figure 6:
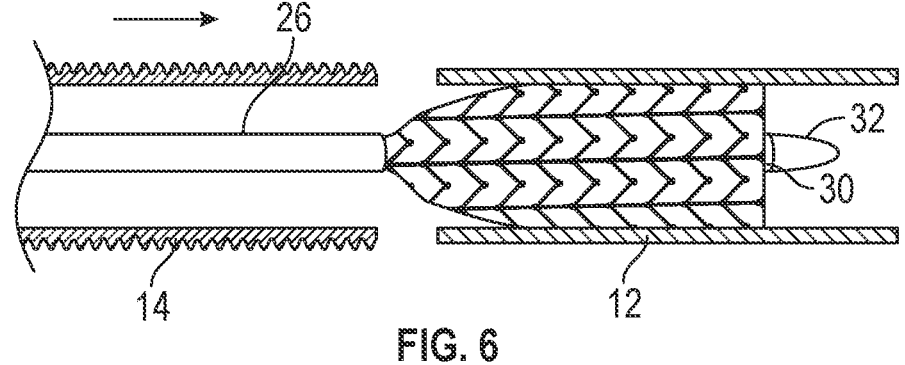
FIG. 6 schematically illustrates advancing a graft over the deployment tool to bring it into proximity with the blood vessel, according to an embodiment of the disclosure.
Figure 7:
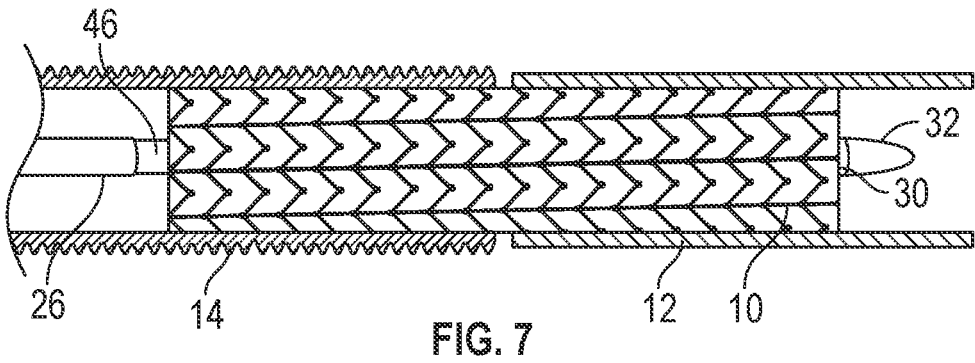
FIG. 7 schematically illustrates further retraction of the outer sheath of the deployment tool to allow expansion of a remaining portion of the vascular connector to secure it within the graft, according to an embodiment of the disclosure.

As an illustration only and without limitation, FIGS. 4-7 schematically depict use of deployment tool 20 to connect vessel 12 to graft 14 with connector 10. As indicated in FIG. 4, deployment tool 20 may be advanced into vessel 12 (potentially over a guidewire routed through lumen 48, although not shown in this view for the sake of clarity) until a desired amount of connector 10 has been disposed within vessel 12, based on visualization or the connector through outer sheath 26, use of marker 52, or a combination of these and other techniques. Next, FIG. 5 schematically indicates the deployment of the distal portion of connector 10 that has been disposed withing vessel 12 as a result of rotation of inner sheath 28. As noted, this may be performed under robotic control by imparting a predetermined amount of rotation via interface 50. As described above, the leadscrew functionality of external threads 40 that are engaged with inner threads 38 of nut drive 24 translate the rotation of inner sheath 28 into a longitudinal motion of outer sheath 26 since it is coupled to nut drive 24. Specifically, rotation of inner sheath 28 in the proper direction causes outer sheath 26 to retract, sequentially exposing connector 10 from its distal end to its proximal end. The coupling joint of ball 42 and socket 44 maintains floating mandrel 30 in the same relative longitudinal position within deployment tool 20 and does not rotate with inner sheath 28. Further, shoulder 46 helps overcome the friction of outer sheath 26 to prevent connector 10 from being displaced longitudinally. As indicated, retraction of outer sheath 26 allows the distal portion of connector 10 that has now been exposed to expand away from floating mandrel 30 from its insertion profile to its deployed profile to engage and secure vessel 12. Next, as indicated in FIG. 6, graft 14 may be advanced coaxially over deployment tool 20 until it is adjacent vessel 12, such as by abutting it or otherwise being in sufficient proximity Now, further rotation of inner sheath 28 causes additional retraction of outer sheath 26 to expose the remaining proximal portion of connector 10 so that it can expand from its insertion profile to its deployed profile to engage and secure graft 14. Deployment tool 20 can now be withdrawn proximally, leaving connector 12 in place to connect vessel 12 and graft 14. Although the embodiment shown in FIGS. 4-7 is discussed in the context of joining vessel 12 and graft 14 in an end-to-end configuration, the techniques can also be applied to join any combination of vessels, grafts or other lumens that conduct the patient's blood and may also be used with an intra-vascular approach through an opening formed in a sidewall of a vessel, graft or other lumen.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the claims and their legal equivalents.

What is claimed is:

1. A vascular connector deployment tool, comprising:
a housing;
an inner sheath extending distally from the housing, wherein the inner sheath is rotatable with respect to the housing;
a floating mandrel;
a connector coupling the floating mandrel to a distal end of the inner sheath such that the inner sheath is capable of rotation with respect to the floating mandrel;
a vascular connector disposed coaxially about the floating mandrel;
an outer sheath telescopically deployed over the inner sheath, wherein the outer sheath is configured to constrain the vascular connector around the floating mandrel in an insertion profile when the outer sheath is disposed over the vascular connector; and
a drive disposed within the housing that is coupled to a proximal end of the outer sheath and is configured to translate a rotational motion of the inner sheath into a longitudinal motion of the outer sheath.

2. The vascular connector deployment tool of claim 1, wherein the drive is coaxially disposed over a proximal portion of the inner sheath and engages external threads on the proximal portion of the inner sheath.

3. The vascular connector deployment tool of claim 2, wherein the drive travels along guides in the housing that permit longitudinal motion and resist rotational motion.

4. The vascular connector deployment tool of claim 2, wherein the drive is configured to translate a first predetermined amount of rotation of the inner sheath into a first known amount of longitudinal motion of the outer sheath.

5. The vascular connector deployment tool of claim 4, wherein the first known amount of longitudinal motion exposes a distal portion of the vascular connector.

6. The vascular connector deployment tool of claim 5, wherein the drive is configured to translate a second predetermined amount of rotation of the inner sheath into a second known amount of longitudinal motion of the outer sheath and wherein the second known amount of longitudinal motion exposes a proximal portion of the vascular connector.

7. The vascular connector deployment tool of claim 4, wherein the inner sheath has an interface that extends from a proximal end of the housing and is configured to rotate the inner sheath.

8. The vascular connector deployment tool of claim 1, wherein the floating mandrel comprises a shoulder configured to engage and resist proximal longitudinal motion of the vascular connector when the outer sheath is retracted.

9. The vascular connector deployment tool of claim 1, wherein the vascular connector is visible through the outer sheath.

10. The vascular connector deployment tool of claim 1, wherein the outer sheath comprises a marker configured to indicate a position of the vascular connector prior to retraction of the outer sheath.

11. The vascular connector deployment tool of claim 1, wherein the vascular connector is a self-expanding connector and is able to maintain radial force at a temperature in a range of 19° C. to 37° C.

12. The vascular connector deployment tool of claim 1, wherein the floating mandrel and the inner sheath comprise a guidewire lumen.

13. A method for implanting a vascular connector in a patient, comprising: providing a vascular connector deployment tool including a housing, an inner sheath extending distally from the housing, wherein the inner sheath is rotatable with respect to the housing, a floating mandrel, a connector coupling the floating mandrel to a distal end of the inner sheath such that the inner sheath is capable of rotation with respect to the floating mandrel, a vascular connector disposed coaxially about the floating mandrel, an outer sheath telescopically deployed over the inner sheath, wherein the outer sheath is configured to constrain the vascular connector around the floating mandrel in an insertion profile when the outer sheath is disposed over the vascular connector, and a drive disposed within the housing that is coupled to a proximal end of the outer sheath and is configured to translate a rotational motion of the inner sheath into a longitudinal motion of the outer sheath; positioning at least a distal portion of the vascular connector within a first lumen for conducting blood of the patient, the vascular connector being constrained around the floating mandrel in an insertion profile; rotating the inner sheath to cause the drive to translate the rotational movement of the inner sheath to longitudinal movement of the outer sheath to cause the outer sheath to retract longitudinally relative to the floating mandrel and expose a distal portion of the vascular connector; and
securing the distal portion of the vascular connector within the first lumen by expansion of the portion of the vascular connector from the insertion profile.

14. The method of claim 13, wherein rotating the inner sheath comprises imparting a first predetermined amount of rotation to cause a first known amount of longitudinal motion of the outer sheath, such that the first known amount of longitudinal motion exposes the distal portion of the vascular connector.

15. The method of claim 14, further comprising: advancing a second lumen for conducting blood of the patient coaxially over the deployment tool until an end of the second lumen is adjacent the opening of the first lumen; further rotating the inner sheath to cause the outer sheath to retract relative to the floating mandrel and expose a remaining portion of the vascular connector; and securing the remaining portion of the vascular connector within the second lumen by expansion of the remaining portion of the vascular connector from the insertion profile.

16. The method of claim 15, wherein further rotating the inner sheath comprises imparting a second predetermined amount of rotation of the inner sheath to cause a second known amount of longitudinal motion of the outer sheath, such that the second known amount of longitudinal motion exposes the remaining portion of the vascular connector, wherein the remaining portion of the vascular connector comprises a proximal portion of the vascular connector.

17. The method of claim 15, wherein the first lumen is a blood vessel and the second lumen is a graft.

18. The method of claim 13, wherein positioning at least the distal portion of the vascular connector within the first lumen comprises visualizing the vascular connector through the outer sheath.

19. The method of claim 13, wherein positioning at least the distal portion of the vascular connector within the first lumen comprises using a marker that indicates a position of the vascular connector prior to retraction of the outer sheath.

\* \* \* \* \*